United States Patent [19]

Francis et al.

[11] Patent Number: 5,072,720
[45] Date of Patent: Dec. 17, 1991

[54] VAGINAL SPECULUM

[76] Inventors: Walter C. Francis, 1837 Kensington Dr., Hampton, Va. 23663; E. William Francis, 1901 Woodfield Dr., Columbia, S.C. 29223

[21] Appl. No.: 461,626

[22] Filed: Jan. 8, 1990

[51] Int. Cl.⁵ .............................................. A61B 1/32
[52] U.S. Cl. ...................................... 128/17; 606/198
[58] Field of Search ............................ 128/17, 18, 20; 606/198

[56] References Cited

U.S. PATENT DOCUMENTS

| | | | |
|---|---|---|---|
| 3,246,646 | 4/1966 | Murphy | 128/17 |
| 3,426,749 | 2/1969 | Jephcott | 128/17 |
| 3,568,665 | 3/1971 | Lindgren | 128/17 |
| 3,716,047 | 2/1973 | Moore et al. | 128/18 |
| 3,752,149 | 8/1973 | Ungar et al. | 128/20 |
| 3,817,242 | 6/1974 | Uddenberg | 128/20 |
| 3,841,317 | 10/1974 | Awais | 128/17 |
| 3,851,642 | 12/1974 | McDonald | 128/18 |
| 3,890,961 | 6/1975 | Moore et al. | 128/17 |
| 3,985,125 | 10/1976 | Rose | 128/17 |
| 4,263,898 | 4/1981 | Wannag | 128/17 |
| 4,492,220 | 1/1985 | Hayes | 128/17 |
| 4,597,382 | 7/1986 | Perez | 128/17 |
| 4,615,334 | 10/1986 | Jaeger | 128/17 |
| 4,766,887 | 8/1988 | Cecil | 128/17 |
| 4,807,600 | 2/1989 | Hayes | 128/17 |

Primary Examiner—Edward M. Coven
Assistant Examiner—Mark S. Graham
Attorney, Agent, or Firm—Wallace J. Nelson

[57] ABSTRACT

A vaginal speculum having padded surfaces on the patient contacting area of the blades thereof serving to minimize patient discomfort and shock immediately prior to and during gynecological examination and/or treatment. A smooth and essentially silent, cam action, mechanism is also provided for opening and locking the instrument in open position.

3 Claims, 3 Drawing Sheets

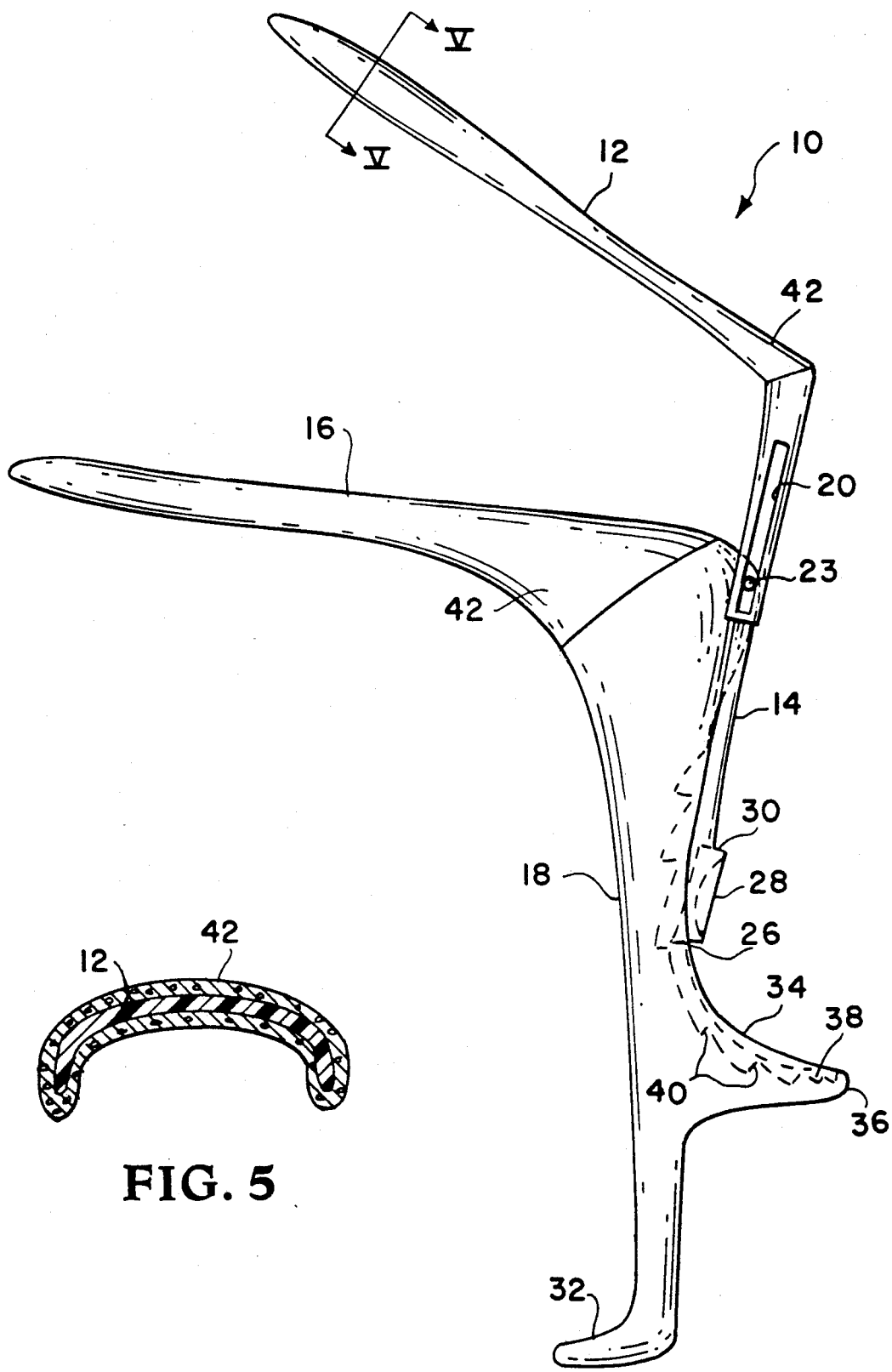

VAGINAL SPECULUM

FIELD OF THE INVENTION

This invention relates generally to medical and surgical instruments and relates specifically to a vaginal speculum adapted to minimize patient discomfort during vaginal examination, as well as during medical and/or surgical treatments.

BACKGROUND OF THE INVENTION

In the examination of interior body cavities of the human body, it is often necessary to employ an instrument to dilate or enlarge these cavities. There are numerous variations and designs for specula that perform this function. Many of these specula are formed of stainless steel or like material that permit sterilization before and after use in an autoclave. Other specula are formed of disposable plastics, sterilized when manufactured or packaged, and discarded after a single use. Dilation of the vagina with a metal or hard plastics speculum can be a shocking and painful experience to patients suffering from a major gynecological disease such as endometriosis, and various forms of cancer, as well as to pre-intercourse or young virgins. The various specula presently available for this purpose, for the most part, perform adequately for the examining physician but have not been designed with the comfort of the patient in mind.

It is therefore an object of the present invention to provide an improved vaginal speculum having a deformable or compressible covering over the speculum blades adapted to contact the vaginal cavity of a patient.

Another object of the present invention is a vaginal speculum that opens at an angle compatible with the organ to reduce the trauma of a vaginal examination.

A further object of the present invention is a vaginal speculum having an improved opening and locking mechanism.

An additional object of the present invention is a vaginal speculum that has patient contacting surfaces that minimize patient discomfort during a vaginal examination.

A further object of the present invention is a vaginal speculum having material surfaces that require minimum lubrication for use thereof.

Another object of the present invention is a vaginal speculum having an opening and locking mechanism that is vibration free and relatively silent in operation.

A further object of the present invention is a deformable or compressible covering for the speculum blades of a vaginal speculum that may be applied by spray coating or dipping existing speculum blades.

SUMMARY OF THE INVENTION

According to the present invention the foregoing and additional objects are attained by providing a vaginal speculum having a pair of duck-bill blades attached to individual handles and adapted to open vertically about a slidable pivot point connection on the instrument handles in a smooth and essentially silent, vibration free, cam action, motion. A patient contacting padded surface is provided on each of the speculum blades to minimize patient discomfort during an examination and/or treatment. The padded surfaces are formed of a foam rubber, silicone gel or similar compressible material with, or without, a plastics or rubber exterior coating that may be readily lubricated by water for ease of insertion into the vagina. The padded surfaces may be formed separately and adhesively or otherwise secured to the speculum blades or the padded surfaces may be integrally formed on existing speculum blades by spraying, dipping or by other conventional applications. Removable padded surfaces may be separately disinfected for re-use, while fixed padded surfaces may be formed of a material that is suitable for autoclaving with the instrument.

BRIEF DESCRIPTION OF THE DRAWINGS

A more complete appreciation of the invention and many of the attendant advantages thereof will be more readily apparent as the same becomes better understood with reference to the following drawings wherein:

FIG. 2 is a view of the speculum shown in FIG. 1 in the open or examination position;

FIG. 5 is a sectional view of one of the speculum blades taken along line V—V of FIG. 2;

DETAILED DESCRIPTION OF THE INVENTION

Figures 1, 3, 6:
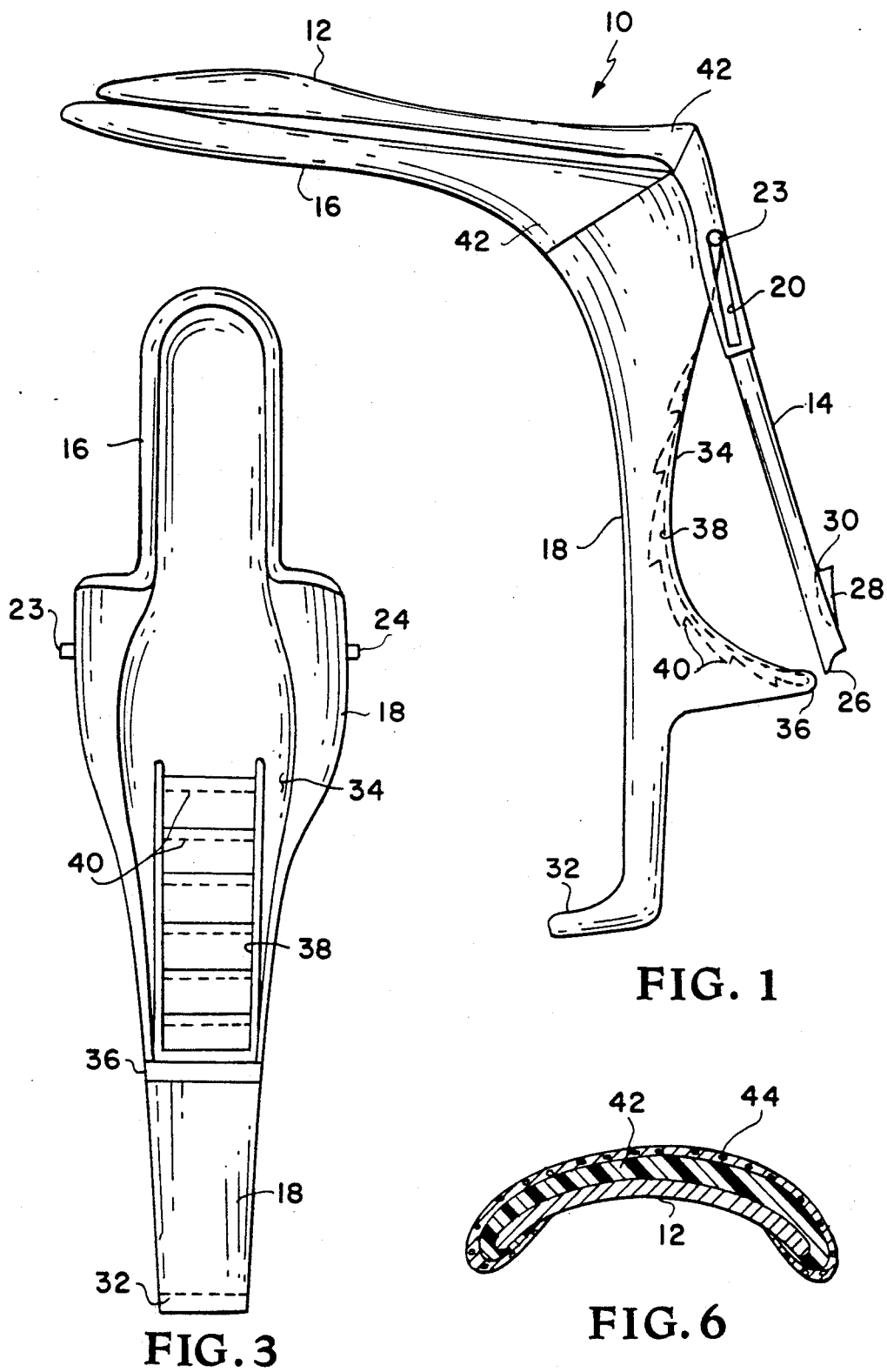
FIG. 1 is a side view of a vaginal speculum according to the present invention in the closed position or insertion mode.
FIG. 3 is a rear view of the bottom blade and handle for the instrument shown in FIGS. 1 and 2.
FIG. 6 is a view similar to FIG. 5 illustrating a modified cushion pad for the speculum blades as seen in section near the tip portion of one of the speculum blades.
Figure 4:
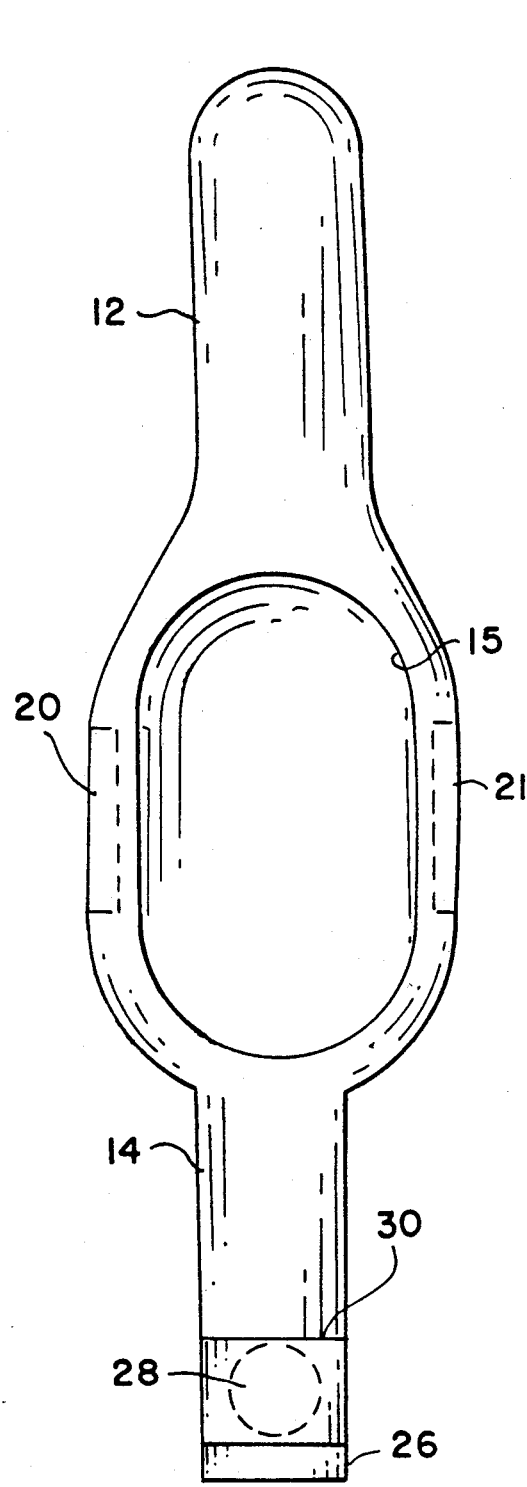
FIG. 4 is a rear view of the top blade and handle for the instrument shown in FIGS. 1 and 2.

Referring now to the drawings and more particularly to FIG. 1, there is shown a vaginal speculum according to the present invention in the closed or insertion mode, and designated generally by reference numeral 10. Speculum 10 is a two-piece, duck-bill type, instrument and includes a top blade 12 having a depending handle 14 integrally extending at a substantially ninety degree angle therefrom, and a bottom blade 16 having a depending handle 18 integrally extending at a substantially ninety degree angle therefrom and in the same direction as blade 12. Handle 14 for blade 12 is provided with a pair of side slots 20,21. As illustrated in FIG. 4, slots 20,21 are disposed, one on each side, at an enlarged portion of handle 14 and serve to slidable and pivotally connect with a pair of pivot pins 23,24 (FIG. 3) extending, one each, from the sides of the upper portion of bottom handle 18, as will be further explained hereinafter. The area of handle 14 adjacent blade 12 is provided with an enlarged oval opening 15 therethrough to permit viewing and treatment of the vaginal cavity by the attending physician, as will be further explained hereinafter. The end of top handle 14 terminates in a relatively sharp tip 26 with a thumb depression 28 being provided on a raised aft portion 30 thereof.

Bottom handle 18 has a curved portion leading from the bottom of blade 16 and merging with a relatively straight front surface that extends the major length thereof. Handle 18 terminates in an integral foot 32 angularly directed in substantially the same direction as blade 16. The aft surface of handle 18 is provided with a concave surface 34 beginning from a point below pivot pins 23,24 and terminating at an extension 36 extending at an angle of essentially ninety degrees aft of the vertical portion of handle 18 and spaced from the tip of handle 18. A groove 38 is provided in concave surface 34 along the length thereof with a plurality of spaced reverse angle transverse slots 40 being provided along the length of groove 38, the purpose of which will be further explained hereinafter.

Each of blades 12 and 16 are provided with a soft compressible cover to reduce the discomfort to a patient when instrument 10 is employed for medical examination and/or treatment. FIG. 5 illustrates a sectional view of blade 12 having a cushion covering 42 thereon. Only the blade covering for blade 12 is described herein in the interest of brevity, but it is to be understood that blade 16 is provided with an identical covering material. Cushion covering 42 is formed of a soft compressible material, such for example as a silicone gel, compressible urethane or polyurethane foam rubber, various latex or latex foam materials, silicones, or other plastics that are soft and easily compressed for shock absorbing properties. These materials may be used alone or provided with an exterior surface covering 44 (FIG. 6). The entire surface of blades 12 and 16 may be covered with the cushion covering material as illustrated in FIG. 5 or only a portion of the blades may be covered as illustrated in FIG. 6.

As shown in FIG. 6, all portions of blade 12 (and 16) that may contact the patient are provided with the cushion covering but the interior of the blades are left uncovered to maximize utilization of the examination/treatment area between blades 12 and 16. Exterior surface covering 44 is formed of a suitable latex, Teflon (polytetrafluoroethylene) or similar material and may be in the form of a film adhesively attached to, or spray or dip coated, and cured directly onto cushioning material 42. Cushioning material 42, with or without exterior cover 44, may be permanently secured via heat resistant adhesive, or the like, to blade 12 (and 16) or may be formed as a removable sleeve for the respective blades. In either case, cushioning material 42 and exterior cover 44 must be heat resistant to the extent that sterilization thereof by autoclaving may be achieved. The exterior surface of cushion material 42, whether it is formed of covering 44 or when used alone, also must have the physical property characteristic of permitting lubrication by sterile water to facilitate use thereof. This is necessary since the use of various lubricating jellies or oil base compositions may contaminate or otherwise interfere with collection of specimens during gynecological examinations. When employing exterior covering 44, the cushioning material 42 may be in the form of a silicone gel or similar readily flowable material. The invention is adaptable for both disposable plastic and stainless steel specula.

Figure 7:
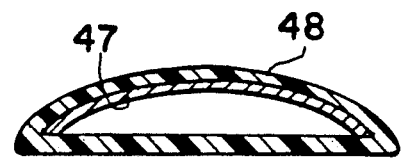
FIG. 7 is a sectional view of one of the speculum blades similar to FIGS. 5 and 6 and showing a further modification of the cushion employed thereon.

When using either a stainless steel, or a plastic, speculum it may be desirable to have the comfort inducing covering formed as a removable sleeve to permit removal and independent sterilization thereof for reuse. FIG. 7 illustrates this embodiment wherein a removable sleeve 48 forms a patient comfort inducing covering for speculum blade 47. When a disposable plastic speculum is employed the covering material (42, 44, or 48) may be adhered to the instrument and discarded therewith, if so desired. Also, in lieu of solid plastic or metal blade 47, the specula blades may be constructed of one or more elongated plastic or metal tangs with the comfort inducing sleeve covering 48 for the tangs serving as the structural blade surfaces.

Figure 8:
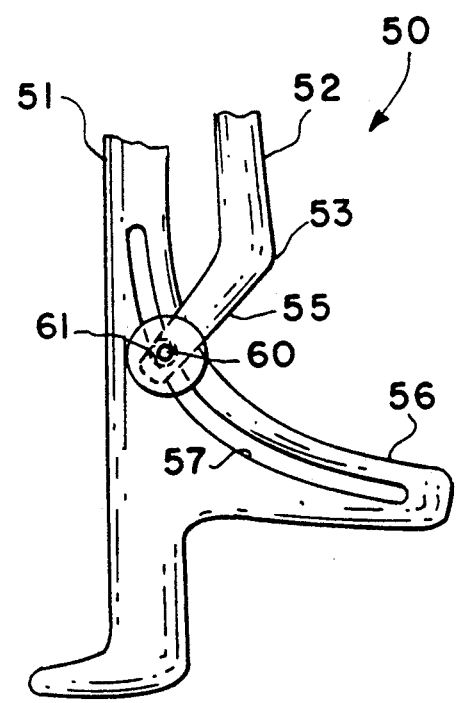
FIG. 8 is a partial view of another speculum, according to the present invention, and illustrating a modification in the speculum opening and closing mechanism.

Referring now to FIG. 8, a modification of the speculum opening and closing mechanism is illustrated and designated generally by reference numeral 50. The top portions of speculum 50 are identical to those of speculum 10 shown in FIG. 1 and are not shown or described further in the interest of brevity. Speculum 50 includes a bottom blade handle 51 and a top blade handle 52. Top blade handle 52 is provided with a thumb depression 53 on one side of the tip end thereof, as in the previously described embodiment. A bifurcated tang 55 angularly extends from the tip end of handle 52 opposite to thumb depression 53. Bifurcated tang 55 slidably receives a portion of bottom handle 51. A cam slot 57 extends along a curved or concave portion 56 of handle 51 and slidably receives a bolt 60 transversely therethrough. Bolt 60 has a head portion recessed, or otherwise conventionally fixed against turning, within a surface of one leg of bifurcated tang 55. The other end of bolt 60 extends through cam slot 57 and the other leg of bifurcated tang 55 and threadingly receives a knurled surfaced nut 61, as will be further explained hereinafter.

In operation, speculum 10 is initially in the position shown in FIG. 1, lubricated by sterile water and inserted into the vagina. After rotation of instrument 10 to the desired position, the physician exerts thumb pressure on handle 14 via raised aft portion 30 to effect relative vertical, and pivotal, movement thereof with consequent separation of blades 12 and 14. Handle 14 moves in a smooth fashion until the desired slot 40 in groove 38 of handle 18 is reached. The examining physician normally has a predetermined slot 40 (along groove 38) in mind for the needed procedure prior to insertion of instrument 10 into the patient. Thus, the physician is able to move handle 14 in one smooth motion to this slot and avoid the clicking and/or vibration associated therewith in use of some prior art specula. Once the desired separation of the blades is obtained, tip 26 of handle 14 is permitted to move into the appropriate slot 40. The pressure of the patient muscles will normally retain instrument 10 in this locked position to permit the examining physician to use both hands, if needed, for his examination and/or treatment through opening 15 of handle 14 and the cavity provided through separated blades 12 and 16.

The simultaneous vertical and pivotal movement of blades 12 and 16 is permitted by the interaction of pivot pins 23,24 within slots 20,21. Additional spaced, reverse angle, transverse cuts may be provided along slots 20,21 to receive pivot pins 23, 24 and assist in retention of instrument 10 in the open position, when so desired. This type movement for a vaginal speculum is far more comfortable to the patient than a fixed pivotal connection for duck-bill specula sometimes employed.

The embodiment illustrated in FIG. 8 operates in a similar manner except that slots 40 are eliminated from top handle 52 and all clicking and vibrations are thus eliminated. In this embodiment, when the instrument 50 has been opened to the desired position, knurled nut 61 is tightened to retain instrument 50 locked in position. The tightening of knurled nut 61 causes the legs of bifurcated tang 55 to fictionally engage the surface of handle 51 and prevent further relative movement between handles 51 and 52 and thereby retain speculum 50 in the desired open position.

When the patient contacting surface of a speculum is metal or hard plastic, there is a shock to the patient whereas with the cushioning foam covering of the present invention, the speculum blades are more consistent with human tissue and results in less shock and less discomfort to the patient during an examination and/or treatment. The present invention also serves to eliminate thermal shock to the patient caused by the use of a cold instrument. Thus, the present invention eliminates the need for heating trays or drawers that are employed by some physicians for vaginal specula. Also, the cam action of the present invention is compatible with the organ and the locking device can be used with only one final click (FIG. 1), or no clicks (FIG. 8), and with essentially no vibration being detectable by the patient.

No specific dimensions have been described for the cushioning material employed in the present invention, it being understood that the thickness of the material may vary for different materials and can also vary at different locations on the instrument blades. For example, when employing silicone coatings the thickness would normally be approximately one-eighth of an inch while the thickness for foam materials can be a quarter of an inch or more. In some instances, the cushioning material thickness may increase the width of the speculum blades to such an extent that the physician must resort to a smaller size instrument than that normally used on a particular patient. Smaller speculum blades than that now employed on the instruments sized "small" may also need to be constructed in practice of the present invention on small women and pre-intercourse or virgin patients. Also, it may be desirable to provide the cushioning material of flesh or other aesthetic colors to minimize the visual shock some patients experience at the sight of any medical instrument.

Thus, although the invention has been described relative to specific embodiments thereof, it is not so limited and there are numerous variations and modifications of the present invention that will be readily apparent to those skilled in the art without departing from the spirit and scope of the appended claims. For example, in the embodiment of FIG. 8, bifurcated tang 55 could be replaced by a single centrally disposed tang with a vertical groove, merging with transverse cam slot 57 along concave portion 56 of handle 51, provided for slidably receiving the centrally disposed tang. Bolt 60 would then be fixed at one end to handle 51 to prevent turning thereof and tightening of knurled nut 61 would frictionally retain the centrally disposed tang against the sides of handle 51.

Other variations and modifications of the invention will be readily apparent to those skilled in the art in the light of the above teachings. It is therefore to be understood that the invention may be practiced other than as specifically described herein.

What is claimed as new and desired to be secured by Letters Patent of the United States is:

1. A vaginal speculum comprising:
a first handle having an integral dilator blade angularly extending from one end thereof;
a second handle having an integral dilator blade angularly extending from one end thereof;
means for connecting said first and said second handles to position said blades in vertical slidable and pivotal contact with each other;
cushioning means disposed on each of said blades to minimize patient discomfort during vaginal examination and treatment;
said cushioning means including a silicone gel covering at least the surface of each of said dilator blades that are adapted to contact the patient; and
a polytetrafluoroethylene covering disposed about said silicone gel.

2. The vaginal speculum of claim 3 including:
said first handle having a concave curved cam surface adjacent an end thereof;
a curved cam slot disposed within said curved cam surface;
means carried by said second handle for slidably engaging said cam slot;
locking means for selectively locking said first and said second handles against relative movement to maintain said speculum in an open position;
said means carried by said second handle for slidably engaging said cam slot including a bifurcated tang angularly extending from the tip of said second handle;
said bifurcated tang being slidably disposed about said concave curved surface of said first handle;
a threaded bolt extending through the ends of said bifurcated tang and said cam slot and serving as said means carried by said second handle for slidably engaging said cam slot; and
a knurled nut threadingly positioned on said threaded bolt and serving as said locking means for selectively locking said first and said second handles against relative movement to maintain said speculum in an open position.

3. A vaginal speculum comprising:
a first handle having an integral dilator blade angularly extending from one end thereof:
a second handle having an integral dilator blade angularly extending from one end thereof:
means for connecting said first and said second handles to position said blades in vertical slidable and pivotal contact with each other;
cushioning means disposed one each of said blades to minimize patient discomfort during vaginal examination and treatment;
said first handle being integral with and angularly depending from the bottom dilator blade and said second handle being integral with an angularly depending from the top dilator blade;
said first handle being disposed forward of said second handle;
said means for connecting said first and said second handles including a pair of pivot pins extending, one each, from the sides of said first handle, said pivot pins being slidably received in a pair of vertical slots disposed, on each, on an enlarged portion of said second handle;
an oval opening disposed through said second handle adjacent the handle area integral with said top dilator blade;
said first handle having a concave curved cam surface adjacent an end thereof and extending along said first handle toward said bottom dilator blade;
a curved cam slot disposed within said curved cam surface;
means carried by said second handle for slidably engaging said cam slot;
locking means for selectively locking said first and said second handles against relative movement to maintain said speculum in an open position;
said means carried by said second handle for slidably engaging said cam slot including a sharp tip surface provided on said second handle and said locking means for locking said first and said second handles against relative movement including a plurality of transverse grooves having a reverse angular cut and disposed in spaced relationship along said cam slot and serving to receive said sharp tip surface of said second handle;

a raised aft portion provided on a length of said second handle adjacent said sharp tip surface and a thumb depression provided in said raised aft portion;

means permitting an attending physician to exert a force on said thumb depression to cause pivotal separation of said blades while at the same time exerting an upward force on said second blade to cause said second blade to move vertically upward and cause said sharp tip to slide unimpeded along said slot in said curved cam surface of said first handle and, when the attending physician releases the force, cause said sharp tip of said second handle to engage one of said transverse grooves in said cam slot and lock said speculum in the open position.

* * * * *